(12) United States Patent
Tsuzuki et al.

(10) Patent No.: US 11,413,230 B2
(45) Date of Patent: Aug. 16, 2022

(54) PROCESS FOR RESHAPING KERATIN FIBERS

(71) Applicant: L'OREAL, Paris (FR)

(72) Inventors: Saki Tsuzuki, Tokyo (JP); Natsumi Komure, Kawasaki (JP)

(73) Assignee: L'OREAL, Paris (FR)

( * ) Notice: Subject to any disclaimer, the term of this patent is extended or adjusted under 35 U.S.C. 154(b) by 50 days.

(21) Appl. No.: 16/754,215

(22) PCT Filed: Oct. 5, 2018

(86) PCT No.: PCT/JP2018/038235
§ 371 (c)(1),
(2) Date: Apr. 7, 2020

(87) PCT Pub. No.: WO2019/074128
PCT Pub. Date: Apr. 18, 2019

(65) Prior Publication Data
US 2021/0186833 A1   Jun. 24, 2021

(30) Foreign Application Priority Data

Oct. 12, 2017 (JP) .............................. JP2017-198290

(51) Int. Cl.
| | |
|---|---|
| *A61K 8/34* | (2006.01) |
| *A61K 8/19* | (2006.01) |
| *A61K 8/46* | (2006.01) |
| *A61Q 5/04* | (2006.01) |

(52) U.S. Cl.
CPC ................ *A61K 8/345* (2013.01); *A61K 8/19* (2013.01); *A61K 8/466* (2013.01); *A61Q 5/04* (2013.01); *A61K 2800/592* (2013.01); *A61K 2800/805* (2013.01)

(58) Field of Classification Search
CPC .................................... A61K 8/34; A61K 8/46
USPC ....................................................... 424/70.2
See application file for complete search history.

(56) References Cited

U.S. PATENT DOCUMENTS

| | | | |
|---|---|---|---|
| 4,459,284 A | | 7/1984 | Azuma et al. |
| 5,520,200 A | * | 5/1996 | Sturla ...................... A45D 7/06 |
| | | | 132/206 |
| 2008/0075681 A1 | * | 3/2008 | Cassier ..................... A61K 8/46 |
| | | | 424/70.2 |
| 2010/0158845 A1 | | 6/2010 | Ellington |
| 2013/0125917 A1 | * | 5/2013 | Janssen ............... C09B 29/3613 |
| | | | 132/208 |

FOREIGN PATENT DOCUMENTS

| | | |
|---|---|---|
| EP | 1880710 A1 | 1/2008 |
| JP | S57-212110 A | 12/1982 |
| JP | 62-009566 B | 2/1987 |
| JP | 2001-512495 A | 8/2001 |
| JP | 2017-537952 A | 12/2017 |
| WO | 2011/155076 A | 12/2011 |
| WO | 2017/018498 A1 | 2/2017 |

OTHER PUBLICATIONS

Translation of Japanese Notice of Reasons for Rejection for counterpart Application No. 2017-198290, dated May 10, 2021.
European Office Action for counterpart Application No. 18796788.0-1112, dated Feb. 4, 2021.
Mintel: "Curl Splash," Kao, Record ID 4358703, Oct. 2016.
Mintel: "Hair Curling Spray," Carver Korea, Record ID 4113611, Aug. 2016.
International Search Report for counterpart Application No. PCT/JP2018/038235, dated Jan. 23, 2019.
Database WPI, Week 198306, Thomson Scientific, London, GB; AN 1983-13789K, XP002787675.

* cited by examiner

*Primary Examiner* — Walter E Webb

(74) *Attorney, Agent, or Firm* — The Marbury Law Group, PLLC

(57) ABSTRACT

The present invention relates to a process for reshaping keratin fibers, preferably hair, comprising the steps of: (i) applying onto the keratin fibers a composition comprising (a) at least one diol selected from $C_{4-5}$ diols, wherein the composition has a pH of from 8.0 to 13.5, preferably from 8.5 to 12.0, and more preferably from 9.0 to 11.0; (ii) heating the keratin fibers; and (iii) optionally rinsing and/or drying the keratin fibers. The present invention can reshape keratin fibers without reducing and oxidizing the keratin fibers, and can provide superior reshaping efficiency, such as strong wave intensity and many curls.

16 Claims, No Drawings

PROCESS FOR RESHAPING KERATIN FIBERS

CROSS REFERENCE TO RELATED APPLICATION

This is a national stage application of PCT/JP2018/038235, filed internationally on Oct. 5, 2018, which claims priority to Japanese Application No. 2017-198290, filed on Oct. 12, 2017, both of which are incorporated by reference herein in their entirety.

TECHNICAL FIELD

The present invention relates to a process, in particular a reshaping process, for keratin fibers such as hair, and a composition, as well as a method and a use, which relate to the process.

BACKGROUND ART

In long-lasting deformation of keratin fibers such as hair, first the disulphide bonds —S—S— of the keratin (cystine) are opened using a composition containing a suitable reducing agent (reduction stage), then the hair thus treated is optionally rinsed; secondly the disulphide bonds are reconstituted by applying, on the keratin fibers previously put under tension (curlers etc.), an oxidizing composition (oxidation stage, also called fixation) so as to finally give the keratin fibers the desired form. This technique thus makes it possible to carry out either waving or straightening of the keratin fibers. For example, JP-B-S62-9566 or U.S. Pat. No. 4,459,284 discloses a standard process for permanent waving or straightening of keratin fibers such as hair in line with the above steps.

The new shape imposed on the keratin fibers by chemical treatment as described above is relatively long-lasting and notably withstands the action of washing with water or shampoo, in contrast to the simple conventional techniques of temporary styling by using foams, styling gels, or lacquers.

Many compositions and processes for the above chemical treatment have been proposed. Generally, they offer good performance on the day of treatment.

However, there are various drawbacks, such as follows, in the above chemical treatment process that may not be suitable from the viewpoint of consumers' or hairdressers' expectations:

Insufficient reshaping efficiency such as weak wave intensity;

Poor usability caused by, for example, long processing time;

High levels of keratin fiber degradation, especially in repeated applications or in combination with other chemical treatments such as oxidative coloration; and Malodor of ammonia or sulfur-containing compounds during and after the deformation process.

In particular, sufficient reshaping efficiency and good usability may be important. There is indeed a need to improve the deformation process of keratin fibers to provide sufficient reshaping efficiency, such as strong wave intensity and many curls of the curled keratin fibers, as well as excellent usability such as short processing time.

In order to improve the usability, a one-step process without reducing or oxidizing was proposed (WO 2011/155076). However, there has been a need to improve reshaping efficiency.

DISCLOSURE OF INVENTION

An objective of the present invention is to provide a new process for reshaping keratin fibers such as hair, which can be performed without reducing or oxidizing the keratin fibers, and can provide the keratin fibers with sufficient reshaping efficiency such as strong wave intensity and many curls.

The above objective of the present invention can be achieved by a process for reshaping keratin fibers, preferably hair, comprising the steps of:

(i) applying onto the keratin fibers a composition comprising
(a) at least one diol selected from $C_{4-5}$ diols, wherein the composition has a pH of from 8.0 to 13.5, preferably from 8.5 to 12.0, and more preferably from 9.0 to 11.0;

(ii) heating the keratin fibers; and (iii) optionally rinsing and/or drying the keratin fibers.

The $C_{4-5}$ diols may be butyleneglycol and pentyleneglycol.

The amount of the (a) diol(s) in the composition may be from 0.01 to 20% by weight, preferably from 0.1 to 15% by weight, and more preferably from more than 1% to 10% by weight, relative to the total weight of the composition.

The composition may further comprise (b) at least one monovalent alcohol, preferably $C_{2-4}$ aliphatic monovalent alcohol, and more preferably ethanol.

The amount of the (b) monovalent alcohol(s) in the composition may be from 0.01 to 20% by weight, preferably from 0.1 to 15% by weight, and more preferably from more than 1% to 10% by weight, relative to the total weight of the composition.

The weight ratio of the amount of the (a) diol/the amount of the (b) monovalent alcohol(s) in the composition may be from 0.1 to 10, preferably from 0.5 to 5, and more preferably from 0.3 to 3.

The composition may further comprise (c) at least one alkaline agent, preferably selected from inorganic alkaline agents except for ammonia, and more preferably selected from alkaline metal hydroxides.

The composition may further comprise (d) at least one organic acid, preferably a monovalent organic acid, more preferably a monovalent sulfonic acid, and more preferably taurine.

The amount of the (d) organic acid(s) in the composition may be from 0.01 to 30% by weight, preferably from 0.1 to 25% by weight, and more preferably from more than 0.5% to 20% by weight, relative to the total weight of the composition.

The composition may further comprise less than 2% by weight, preferably less than 1% by weight, and more preferably less than 0.1% by weight, of a reducing agent.

The process is intended for deforming, preferably temporary or permanent waving, and more preferably permanent waving, of the keratin fibers.

In the process according to the present invention, the keratin fibers may be heated during the heating step to from 50° C. to 180° C., preferably from 70° C. to 150° C., and more preferably from 80° C. to 120° C.

The process according to the present invention may further comprise the step of placing the keratin fibers, before the heating step, in an occlusive space surrounding the keratin fibers to keep the keratin fibers wet.

The present invention also relates to a composition for one-step reshaping of keratin fibers, preferably hair, by heating, comprising:
(a) at least one diol selected from $C_{4-5}$ diols,
wherein
the composition has a pH of from 8.0 to 13.5, preferably from 8.5 to 12.0, and more preferably from 9.0 to 11.0.

The present invention also relates to a method for enhancing reshaping efficiency of keratin fibers as a result of a reshaping process of the keratin fibers with a composition having a pH of 8.0 to 13.5, preferably from 8.5 to 12.0, and more preferably from 9.0 to 11.0, without reducing or oxidizing the keratin fibers, characterized by adding at least one diol selected from $C_{4-5}$ diols to the composition.

The present invention also relates to a use of at least one diol selected from $C_{4-5}$ diols in a composition having a pH of 8.0 to 13.5, preferably from 8.5 to 12.0, and more preferably from 9.0 to 11.0, wherein the composition is used for reshaping keratin fibers without reducing or oxidizing the keratin fibers, for enhancing reshaping efficiency of the keratin fibers.

The process, composition, method and use according to the present invention can be used to reshape or deform keratin fibers, preferably hair, and can provide the keratin fibers with sufficient reshaping efficiency such as strong wave intensity and many curls. Also, the present invention can provide good usability such as short processing time due to the absence of the steps of reducing and oxidizing keratin fibers.

In addition, the present invention can provide keratin fibers with long-lasting volumizing effects. In other words, the present invention can maintain for a long period of time the volume of style of the keratin fibers as a result of reshaping process of the keratin fibers.

BEST MODE FOR CARRYING OUT THE INVENTION

After diligent research, the inventors have found that the use of at least one $C_{4-5}$ diol in an alkaline composition for one-step reshaping of keratin fibers by heating, which does not need to perform reducing and oxidizing of keratin fibers, can enhance the reshaping efficiency, such as strong wave intensity and many curls, of the composition.

Thus, one aspect of the present invention is a process for reshaping keratin fibers, preferably hair, comprising the steps of:
(i) applying onto the keratin fibers a composition comprising
   (a) at least one diol selected from $C_{4-5}$ diols, wherein the composition has a pH of from 8.0 to 13.5, preferably from 8.5 to 12.0, and more preferably from 9.0 to 11.0;
(ii) heating the keratin fibers; and
(iii) optionally rinsing and/or drying the keratin fibers.

Another aspect of the present invention is a composition for one-step reshaping of keratin fibers, preferably hair, by heating, comprising:
(a) at least one diol selected from $C_{4-5}$ diols,
wherein
the composition has a pH of from 8.0 to 13.5, preferably from 8.5 to 12.0, and more preferably from 9.0 to 11.0.

Another aspect of the present invention is a method for enhancing reshaping efficiency of keratin fibers as a result of a reshaping process of the keratin fibers with a composition having a pH of 8.0 to 13.5, preferably from 8.5 to 12.0, and more preferably from 9.0 to 11.0, without reducing or oxidizing the keratin fibers, characterized by adding at least one diol selected from $C_{4-5}$ diols to the composition.

Another aspect of the present invention is a use of at least one diol selected from $C_{4-5}$ diols in a composition having a pH of 8.0 to 13.5, preferably from 8.5 to 12.0, and more preferably from 9.0 to 11.0, wherein the composition is used for reshaping keratin fibers without reducing or oxidizing the keratin fibers, for enhancing reshaping efficiency of the keratin fibers.

The present invention can reshape keratin fibers without reducing and oxidizing the keratin fibers, and can provide superior reshaping efficiency, such as strong wave intensity and many curls. For example, the process according to the present invention can reshape keratin fibers such as hair, in one step (without reducing or oxidizing the keratin fibers) and can provide the keratin fibers with sufficient reshaping efficiency such as strong wave intensity and many curls.

Hereafter, the process, composition, method and use according to the present invention will each be described in a detailed manner.

[Process]

The process according to the present invention is a process for reshaping keratin fibers, preferably hair, comprising the steps of:
(i) applying onto the keratin fibers a composition comprising
   (a) at least one diol selected from $C_{4-5}$ diols, wherein the composition has a pH of from 8.0 to 13.5, preferably from 8.5 to 12.0, and more preferably from 9.0 to 11.0;
(ii) heating the keratin fibers; and
(iii) optionally rinsing and/or drying the keratin fibers.

The details of the composition used in the process according to the present invention will be explained in the section titled [Composition] below. Thus, the composition used in the process according to the present invention can be the same as the composition according to the present invention.

The process according to the present invention is intended for deforming, preferably temporary or permanent waving, and more preferably permanent weaving, of keratin fibers such as hair.

In step (i), the composition which will be described later is applied to the keratin fibers. The application of the composition may be performed by any means, such as a brush and a comb. It may be possible that the keratin fibers after the application of the composition be left as they are for a certain amount of time typically from 1 minute to 1 hour, preferably from 5 to 10 minutes, if necessary, in order to let the composition penetrate into the keratin fibers.

In step (ii), the keratin fibers are heated.

It may be preferable that the keratin fibers are heated during the (ii) heating step to 50° C. or higher, preferably 70° C. or higher, and more preferably 80° C. or higher.

It may be preferable that the keratin fibers are heated during the (ii) heating step to 180° C. or lower, preferably 150° C. or lower, and more preferably 120° C. or lower.

It may be preferable that the keratin fibers are heated during the (ii) heating step to from 50° C. to 180° C., preferably from 70° C. to 150° C., and more preferably from 80° C. to 120° C. The heating time may be, for example, from 5 to 30 minutes, and preferably from 10 to 20 minutes. The (ii) heating step can be performed by any heating means which can be controlled to realize the temperature desired for the process.

According to the present invention, keratin fibers such as hair may be subjected to mechanical tension, which is typically used for deforming keratin fibers, before and/or after step (i), and preferably before step (ii).

The mechanical tension can be applied to the keratin fibers by any means to deform the keratin fibers to an intended shape. For example, the mechanical tension may be provided by at least one reshaping means selected from the group consisting of a curler, a roller, and a clip. The reshaping means may comprise at least one heater. If the keratin fibers are rolled around a curler, this rolling-up may be performed on the entire length of the keratin fibers or, for example, on half the length of the keratin fibers. Depending on, for example, the desired hairstyle shape and amount of curls, the rolling-up may be performed with more or less thick locks.

It may be preferable that the process according to the present invention comprise the step of placing the keratin fibers, before the (ii) heating step, in an occlusive space surrounding the keratin fibers to keep the keratin fibers wet. If the above deforming step of applying the mechanical tension to the keratin fibers is performed, this placing step can be performed after the deforming step.

The occlusive space may be formed by at least one coating means. The coating means may be rigid or flexible. The coating means may comprise at least one member selected from the group consisting of a film and a sheet. The material of the film or the sheet is not limited. For example, the film or the sheet may comprise a thermoplastic or thermosetting resin, a paper, a textile, a bonnet, a metal foil such as aluminum foil, and the like.

For example, the film or sheet may be set on a heating rod, a heating bar or a heating plate which is covered by keratin fibers, in order to form the occlusive space.

The occlusive space can restrict the evaporation of evaporable components such as water in the composition which has been applied to keratin fibers, and therefore, the temperature of the keratin fibers can be increased higher than that obtainable by a conventional heating process or device for the keratin fibers in open conditions. Furthermore, the keratin fibers can be heated effectively, and the keratin fibers can be heated evenly.

The occlusive space may form a condensation cage in which water and a component or components in the composition used in the process according to the present invention may evaporate from the keratin fibers, adhere to the wall of the coating means, and drop onto the keratin fibers. This cycle may be repeated during the heating of the keratin fibers. Thus, the keratin fibers can always be kept wet, and drying and deterioration of the keratin fibers will be prevented.

The formation of the occlusive space may be preferable because the keratin fibers in the occlusive space can be kept wet and the temperature of the keratin fibers can be kept constant.

The wet conditions of the keratin fibers may be preferable for the ingredients in the composition used in the process according to the present invention to effectively penetrate into the keratin fibers.

In step (iii), the keratin fibers may be rinsed preferably with water, and/or may be dried. The drying of the keratin fibers can be performed with a conventional drying means such as a hair drier.

[Composition]
(Diol)

The composition according to the present invention comprises at least one (a) diol selected from $C_{4-5}$ diols. Two or more diols may be used in combination. Thus, a single type of diol or a combination of different types of diols may be used.

Although not bound by any theory, it is believed that the (a) diol can loosen the hydrophobic interaction between keratin fibers to increase reshaping efficiency.

The $C_{4-5}$ diols can be butyleneglycol and pentyleneglycol.

Butyleneglycol encompasses isomers thereof. Thus, butyleneglycol may be, for example, 1,2-butyleneglycol, 1,3-butyleneglycol, 2,3-butyleneglycol and 1,4-butyleneglycol. 1,3-butyleneglycol may be preferable.

Pentyleneglycol encompasses isomers thereof. Thus, pentyleneglycol may be 1,2-pentyleneglycol, 1,3-pentyleneglycol, 1,4-pentyleneglycol, 1,5-pentyleneglycol, 2,3-pentyleneglycol, and 2,4-penyleneglycol. 1,2-pentyleneglycol may be preferable.

The amount of the (a) diol(s) in the composition according to the present invention may be 0.01% by weight or more, preferably 0.1% by weight or more, more preferably more than 1% by weight, and even more preferably more than 5% by weight, relative to the total weight of the composition.

On the other hand, the amount of the (a) diol(s) in the composition according to the present invention may be 20% by weight or less, preferably 15% by weight or less, and more preferably 10% by weight or less, relative to the total weight of the composition.

The amount of the (a) diol(s) in the composition according to the present invention may range from 0.01% to 20% by weight, preferably from 0.1% to 15% by weight, more preferably from more than 1% to 10% by weight, and even more preferably from more than 5% to 10% by weight, relative to the total weight of the composition.

(Monovalent Alcohol)

The composition according to the present invention may further comprise at least one (b) monovalent alcohol. Two or more such alcohols may be used in combination. Thus, a single type of such alcohol or a combination of different types of such alcohol may be used.

The (b) monovalent alcohol is preferably in the form of a liquid at ambient temperature such as 25° C. under atmospheric pressure (760 mmHg or $10^5$ Pa).

The term "monovalent alcohol" here means an alcohol having one hydroxy group.

The (b) monovalent alcohol may be non-aromatic (aliphatic) or aromatic.

The non-aromatic monovalent alcohol is preferably a saturated or unsaturated, linear or branched lower aliphatic monovalent alcohol, more preferably a $C_2$-$C_6$ aliphatic monovalent alcohol, even more preferably a saturated or unsaturated, linear or branched $C_2$-$C_5$ aliphatic monovalent alcohol, and most preferably a saturated or unsaturated, linear or branched $C_2$-$C_4$ aliphatic monovalent alcohol. Preferred non-aromatic monovalent alcohols are ethanol, isopropanol and mixtures thereof.

The aromatic monovalent alcohol is preferably selected from the group consisting of benzyl alcohol, phenethylalcohol, diphenyl ethanol, cinnamyl alcohol, tryptophol, 3-nitrobenzylalcohol, veratryl alcohol, benzoin and mixtures thereof.

It is preferable that the (b) monovalent alcohol not be a fatty alcohol or higher alcohol.

It is preferable that the (b) monovalent alcohol be selected from the group consisting of lower aliphatic alcohols, aromatic alcohols and mixtures thereof, and more preferably selected from the group consisting of ethanol, benzyl alcohol, and mixtures thereof.

The amount of the (b) monovalent alcohol(s) in the composition according to the present invention may be 0.01% by weight or more, preferably 0.1% by weight or more, more preferably 1% by weight or more, and even more preferably 2.5% by weight or more, relative to the total weight of the composition.

On the other hand, the amount of the (b) monovalent alcohol(s) in the composition according to the present invention may be 20% by weight or less, preferably 15% by weight or less, and more preferably 5% by weight or less, relative to the total weight of the composition.

The amount of the (b) monovalent alcohol(s) in the composition according to the present invention may range from 0.01% to 20% by weight, preferably from 0.1% to 15% by weight, more preferably from 1% to 10% by weight, even more preferably from 2.5% to 5% by weight, relative to the total weight of the composition.

It may be preferable that the weight ratio of the amount of the (a) diol/the amount of the (b) monovalent alcohol(s) in the composition be from 0.1 to 10, more preferably from 0.5 to 5, and even more preferably from 0.3 to 3.

(Alkaline Agent)

The composition according to the present invention may further comprise at least one (c) alkaline agent. Two or more (c) alkaline agents may be used in combination. Thus, a single type of alkaline agent or a combination of different types of alkaline agents may be used.

The (c) alkaline agent at a high temperature may cause lanthionization in keratin fibers which could contribute to reshaping of the keratin fibers.

The (c) alkaline agent may be an inorganic alkaline agent. It may be possible that the inorganic alkaline agent be selected from the group consisting of ammonia; alkaline metal hydroxides; alkaline earth metal hydroxides; alkaline metal phosphates and monohydrogenophosphates such as sodium phosphate or sodium monohydrogenophosphate. However, it is preferable that the (c) alkaline agent not be ammonia because of the odor thereof. Thus, it is preferable that the inorganic alkaline agent be selected from inorganic ammonium salts such as ammonium carbonate and ammonium bicarbonate; and alkylammonium hydroxides such as tetramethylammonium hydroxide.

As examples of the inorganic alkaline metal hydroxides, mention may be made of sodium hydroxide and potassium hydroxide. As examples of the alkaline earth metal hydroxides, mention may be made of calcium hydroxide and magnesium hydroxide. As the inorganic alkaline agent, sodium hydroxide is preferable.

The alkaline agent may be an organic alkaline agent. It is preferable that the organic alkaline agent be selected from the group consisting of monoamines and derivatives thereof; diamines and derivatives thereof; polyamines and derivatives thereof; basic amino acids and derivatives thereof; oligomers of basic amino acids and derivatives thereof; polymers of basic amino acids and derivatives thereof; urea and derivatives thereof; and guanidine and derivatives thereof.

As examples of the organic alkaline agents, mention may be made of alkanolamines such as mono-, di- and tri-ethanolamine, and isopropanolamine; urea, guanidine and their derivatives; basic amino acids such as lysine, ornithine or arginine; and diamines such as those described in the structure below:

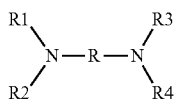

wherein R denotes an alkylene such as propylene optionally substituted by a hydroxyl or a $C_1$-$C_4$ alkyl radical, and $R_1$, $R_2$, $R_3$ and $R_4$ independently denote a hydrogen atom, an alkyl radical or a $C_1$-$C_4$ hydroxyalkyl radical, which may be exemplified by 1,3-propanediamine and derivatives thereof. Arginine, urea and monoethanolamine are preferable.

The amount of the (c) alkaline agent(s) in the composition according to the present invention may be 0.01% by weight or more, preferably 0.1% by weight or more, more preferably 1% by weight or more, and even more preferably 2% by weight or more, relative to the total weight of the composition.

On the other hand, the amount of the (c) alkaline agent(s) in the composition according to the present invention may be 20% by weight or less, preferably 15% by weight or less, more preferably 10% by weight or less, and even more preferably 8% by weight or less, relative to the total weight of the composition.

The amount of the (c) alkaline agent(s) in the composition according to the present invention may range from 0.01% to 20% by weight, preferably from 0.1% to 15% by weight, more preferably from 1% to 10% by weight, and even more preferably from 2% to 8% by weight, relative to the total weight of the composition.

(Organic Acid)

The composition according to the present invention may further comprise at least one (d) organic acid. Two or more (d) organic acids may be used in combination. Thus, a single type of organic acid or a combination of different types of organic acids may be used.

The (d) organic acid may work as a buffering agent to effectively maintain the alkaline condition of the composition according to the present invention.

It may be preferable that the (d) organic acid have a pKa value of less than 3.5. It may be more preferable that the (d) organic acid have a pKa value of from 0.5 to less than 3.5, more preferably from 1.0 to 3.0, and even more preferably from 1.5 to 2.8. The pKa value may be measured at 25° C. The (d) organic acid may have at least one pKa value less than 3.5, and may have two or more pKa values. If the (d) organic acid has two or more pKa values, at least one of the pKa values must be in a range less than 3.5.

One should recall that the term "organic" means that the acid has at least one carbon atom in its chemical structure.

It is preferable that the (d) organic acid be non-volatile. One should recall that the term "non-volatile" means that the acid has a vapor pressure generally lower than 0.02 mmHg (2.66 Pa) at room temperature.

The (d) organic acid may be selected from the group consisting of carboxylic acids, aminosulfonic acids, amino acids such as glycine, alanine, glutamic acid, aspartic acid, phenyl alanine, β-alanine, isoleucine, leucine, proline, glutamine, serine, threonine, valine, tryptophane, tyrosine, oligomers of amino acids such as glycylglycine, and mixtures thereof.

The carboxylic acids may be selected from the group consisting of oxalic acid, malonic acid, maleic acid, salicylic acid, phthalic acid, and mixtures thereof.

The aminosulfonic acid may be selected from the group consisting of taurine, 2-(cyclohexylamino)ethanesulfonic acid, and mixtures thereof.

It is preferable that the (d) organic acid be selected from taurine, 2-(cyclohexylamino)ethanesulfonic acid, glycine, alanine, proline, and mixtures thereof.

The amount of the (d) organic acid(s) in the composition according to the present invention may be 0.01% by weight or more, preferably 0.1% by weight or more, more preferably 0.5% by weight or more, and even more preferably 5% by weight or more, relative to the total weight of the composition.

On the other hand, the amount of the (d) organic acid(s) in the composition according to the present invention may be 30% by weight or less, preferably 25% by weight or less, more preferably 20% by weight or less, and even more preferably 10% by weight or less, relative to the total weight of the composition.

The amount of the (d) organic acid(s) in the composition according to the present invention may range from 0.01% to 30% by weight, preferably from 0.1% to 25% by weight, more preferably from 0.5% to 20% by weight, and even more preferably from 5% to 10% by weight, relative to the total weight of the composition.

(pH)

The pH of the composition according to the present invention is 8.0 or higher, preferably 8.5 or higher, and more preferably 9.0 or higher.

The pH of the composition according to the present invention is 13.5 or lower, preferably 12.0 or lower, and more preferably 11.0 or lower.

The pH of the composition according to the present invention is 8.0 to 13.5, preferably from 8.5 to 12.0, and more preferably from 9.0 to 11.0.

Thus, the composition according to the present invention typically comprises water.

The amount of water in the composition may be from 50 to 99% by weight, preferably from 55 to 95% by weight, and more preferably from 60 to 90% by weight, relative to the total weight of the composition.

(Oil)

The composition according to the present invention may further comprise at least one oil. If two or more oils are used, they may be the same or different.

Here, "oil" means a fatty compound or substance which is in the form of a liquid or a paste (non-solid) at room temperature (25° C.) under atmospheric pressure (760 mmHg). As the oils, those generally used in cosmetics can be used alone or in combination thereof. These oils may be volatile or non-volatile.

The oil may be a non-polar oil such as a hydrocarbon oil, a silicone oil, or the like; a polar oil such as a plant or animal oil and an ester oil or an ether oil; or a mixture thereof.

The oil may be selected from the group consisting of oils of plant or animal origin, synthetic oils, silicone oils, hydrocarbon oils, and fatty alcohols.

As examples of plant oils, mention may be made of, for example, linseed oil, *camellia* oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, coconut oil, and mixtures thereof.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate, and isostearyl neopentanoate.

Esters of $C_4$-$C_{22}$ dicarboxylic or tricarboxylic acids and of $C_1$-$C_{22}$ alcohols, and esters of monocarboxylic, dicarboxylic, or tricarboxylic acids and of non-sugar $C_4$-$C_{26}$ dihydroxy, trihydroxy, tetrahydroxy, or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides, or polysaccharides.

Examples of suitable sugars that may be mentioned include sucrose (or saccharose), glucose, galactose, ribose, fucose, maltose, fructose, mannose, arabinose, xylose, and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters, and polyesters, and mixtures thereof.

These esters may be, for example, oleates, laurates, palmitates, myristates, behenates, cocoates, stearates, linoleates, linolenates, caprates, and arachidonates, or mixtures thereof such as, especially, oleopalmitate, oleostearate, and palmitostearate mixed esters, as well as pentaerythrityl tetraethyl hexanoate.

More particularly, use is made of monoesters and diesters and especially sucrose, glucose, or methylglucose monooleates or dioleates, stearates, behenates, oleopalmitates, linoleates, linolenates, and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate), and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as cyclohexasiloxane, octamethylcyclotetrasiloxane, decamethylcyclopentasiloxane, dodecamethylcyclohexasiloxane, and the like; and mixtures thereof.

Preferably, the silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used in accordance with the present invention are silicone oils as defined above and comprise in their structure one or more organofunctional groups attached via a hydrocarbon-based group.

Organopolysiloxanes are defined in greater detail in Walter Noll's Chemistry and Technology of Silicones (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of the type such as dimethylsiloxane/methylalkylsiloxane, such as Silicone Volatile® FZ 3109 sold by the company Union Carbide, of formula:
with D":

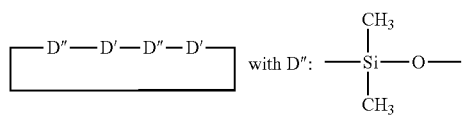

and with D':

$$\text{—Si(CH}_3\text{)(C}_8\text{H}_{17}\text{)—O—}$$

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane; and (ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s; and the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups, mention may be made of polydiarylsiloxanes, especially polydiphenylsiloxanes and polyalkylarylsiloxanes such as phenyl silicone oil.

The phenyl silicone oil may be chosen from the phenyl silicones of the following formula:

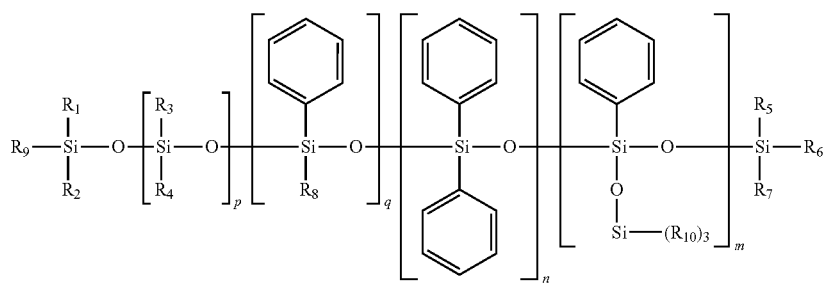

in which $R_1$ to $R_{10}$, independently of each other, are saturated or unsaturated, linear, cyclic or branched $C_1$-$C_{30}$ hydrocarbon-based radicals, preferably $C_1$-$C_{12}$ hydrocarbon-based radicals, and more preferably $C_1$-$C_6$ hydrocarbon-based radicals, in particular methyl, ethyl, propyl, or butyl radicals, and m, n, p, and q are, independently of each other, integers of 0 to 900 inclusive, preferably 0 to 500 inclusive, and more preferably 0 to 100 inclusive, with the proviso that the sum n+m+q is other than 0.

Examples that may be mentioned include the products sold under the following names:

the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
certain oils of the SF series from General Electric, such as SF 1023, SF 1154, SF 1250, and SF 1265.

As the phenyl silicone oil, phenyl trimethicone ($R_1$ to $R_{10}$ are methyl; p, q, and n=0; m=1 in the above formula) is preferable.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:

linear or branched, optionally cyclic, $C_6$-$C_{16}$ lower alkanes. Examples that may be mentioned include hexane, undecane, dodecane, tridecane, and isoparaffins, for instance isohexadecane, isododecane, and isodecane; and
linear or branched hydrocarbons containing more than 16 carbon atoms, such as liquid paraffins, liquid petroleum jelly, polydecenes and hydrogenated polyisobutenes such as Parleam®, and squalane and himi-squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

The term "fatty" in the fatty alcohol means the inclusion of a relatively large number of carbon atoms. Thus, alcohols which have 4 or more, preferably 6 or more, and more preferably 12 or more carbon atoms are encompassed within the scope of fatty alcohols. The fatty alcohol may be saturated or unsaturated. The fatty alcohol may be linear or branched.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may or may not be substituted with at least one hydroxyl group.

As examples of the fatty alcohol, mention may be made of lauryl alcohol, cetyl alcohol, stearyl alcohol, isostearyl alcohol, behenyl alcohol, undecylenyl alcohol, myristyl alcohol, octyldodecanol, hexyldecanol, oleyl alcohol, linoleyl alcohol, palmitoleyl alcohol, arachidonyl alcohol, erucyl alcohol, and mixtures thereof.

It is preferable that the fatty alcohol be a saturated fatty alcohol.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term "saturated fatty alcohol" here means an alcohol having a long aliphatic saturated, carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of lauryl alcohol, cetyl alcohol, stearyl alcohol, isostearyl alcohol, behenyl alcohol, undecylenyl alcohol, myristyl alcohol, octyldodecanol, hexyldecanol, and mixtures thereof. In one embodiment, cetyl alcohol, stearyl alcohol, octyldodecanol, hexyldecanol, or a mixture thereof (e.g., cetearyl alcohol) as well as behenyl alcohol, can be used as a saturated fatty alcohol.

According to at least one embodiment, the fatty alcohol used in the composition according to the present invention is preferably chosen from cetyl alcohol, octyldodecanol, hexyldecanol, and mixtures thereof.

It may be preferable that the oil be chosen from hydrocarbon oils such as mineral oil and silicone oils such as dimethicone.

The amount of the oil in the composition according to the present invention may be 0.01% by weight or more, preferably 0.05% by weight or more, more preferably 0.1% by weight or more, and even more preferably 0.2% by weight or more, relative to the total weight of the composition.

On the other hand, the amount of the oil in the composition according to the present invention may be 20% by weight or less, preferably 15% by weight or less, more preferably 10% by weight or less, and even more preferably 5% by weight or less, relative to the total weight of the composition.

The amount of the oil in the composition according to the present invention may range from 0.01% to 20% by weight, preferably from 0.05% to 15% by weight, more preferably from 0.1% to 10% by weight, even more preferably from 0.2% to 5% by weight, relative to the total weight of the composition.

(Surfactant)

The composition according to the present invention may further comprise at least one surfactant. Two or more surfactants may be used. Thus, a single type of surfactant or a combination of different types of surfactants may be used.

Any surfactant may be used for the present invention. The surfactant may be selected from the group consisting of anionic surfactants, amphoteric surfactants, cationic surfactants and nonionic surfactants. Two or more surfactants may be used in combination. Thus, a single type of surfactant or a combination of different types of surfactants may be used.

According to one embodiment of the present invention, the amount of the surfactant(s) may range from 0.01 to 15% by weight, preferably from 0.05 to 10% by weight, and more preferably from 0.1 to 5% by weight, relative to the total weight of the composition used in the process according to the present invention.

(i) Anionic Surfactants

The composition may comprise at least one anionic surfactant. Two or more anionic surfactants may be used in combination.

It is preferable that the anionic surfactant be selected from the group consisting of ($C_6$-$C_{30}$)alkyl sulfates, ($C_6$-$C_{30}$)alkyl ether sulfates, ($C_6$-$C_{30}$)alkylamido ether sulfates, alkylaryl polyether sulfates, monoglyceride sulfates; ($C_6$-$C_{30}$)alkylsulfonates, ($C_6$-$C_{30}$)alkylamide sulfonates, ($C_6$-$C_{30}$)alkylaryl sulfonates, α-olefin sulfonates, paraffin sulfonates; ($C_6$-$C_{30}$)alkyl phosphates; ($C_6$-$C_{30}$)alkyl sulfosuccinates, ($C_6$-$C_{30}$)alkyl ether sulfosuccinates, ($C_6$-$C_{30}$)alkylamide sulfosuccinates; ($C_6$-$C_{30}$)alkyl sulfoacetates; ($C_6$-$C_{24}$)acyl sarcosinates; ($C_6$-$C_{24}$)acyl glutamates; ($C_6$-$C_{30}$)alkylpolyglycoside carboxylic ethers; ($C_6$-$C_{30}$)alkylpolyglycoside sulfosuccinates; ($C_6$-$C_{30}$)alkyl sulfosuccinamates; ($C_6$-$C_{24}$) acyl isethionates; N—($C_6$-$C_{24}$)acyl taurates; $C_6$-$C_{30}$ fatty acid salts; coconut oil acid salts or hydrogenated coconut oil acid salts; ($C_8$-$C_{20}$)acyl lactylates; ($C_6$-$C_{30}$)alkyl-D-galactoside uronic acid salts; polyoxyalkylenated ($C_6$-$C_{30}$)alkyl ether carboxylic acid salts; polyoxyalkylenated ($C_6$-$C_{30}$) alkylaryl ether carboxylic acid salts; and polyoxyalkylenated ($C_6$-$C_{30}$)alkylamido ether carboxylic acid salts; and corresponding acid forms.

In at least one embodiment, the anionic surfactants are in the form of salts such as salts of alkali metals, for instance sodium; salts of alkaline-earth metals, for instance magnesium; ammonium salts; amine salts; and amino alcohol salts. Depending on the conditions, they may also be in acid form.

It is more preferable that the anionic surfactant be selected from salts of ($C_6$-$C_{30}$)alkyl sulfate, ($C_6$-$C_{30}$)alkyl ether sulfate or polyoxyalkylenated ($C_6$-$C_{30}$)alkyl ether carboxylic acid, salified or not.

(ii) Amphoteric Surfactants

The composition may comprise at least one amphoteric surfactant. Two or more amphoteric surfactants may be used in combination.

The amphoteric or zwitterionic surfactants can be, for example (non-limiting list), amine derivatives such as aliphatic secondary or tertiary amine, and optionally quaternized amine derivatives, in which the aliphatic radical is a linear or branched chain including 8 to 22 carbon atoms and containing at least one water-solubilizing anionic group (for example, carboxylate, sulphonate, sulphate, phosphate or phosphonate).

The amphoteric surfactant may preferably be selected from the group consisting of betaines and amidoaminecarboxylated derivatives.

It is preferable that the amphoteric surfactant be selected from betaine-type surfactants.

The betaine-type amphoteric surfactant is preferably selected from the group consisting of alkylbetaines, alkylamidoalkylbetaines, sulfobetaines, phosphobetaines, and alkylamidoalkylsulfobetaines, in particular, ($C_8$-$C_{24}$)alkylbetaines, ($C_8$-$C_{24}$)alkylamido($C_1$-$C_8$)alkylbetaines, sulphobetaines, and ($C_8$-$C_{24}$)alkylamido($C_1$-$C_8$)alkylsulphobetaines. In one embodiment, the amphoteric surfactants of betaine type are chosen from ($C_8$-$C_{24}$)alkylbetaines, ($C_8$-$C_{24}$)alkylamido($C_1$-$C_8$)alkylsulphobetaines, sulphobetaines, and phosphobetaines.

Non-limiting examples that may be mentioned include the compounds classified in the CTFA International Cosmetic Ingredient Dictionary & Handbook, 15th Edition, 2014, under the names cocobetaine, laurylbetaine, cetylbetaine, coco/oleamidopropylbetaine, cocamidopropylbetaine, palmitamidopropylbetaine, stearamidopropylbetaine, cocamidoethylbetaine, cocamidopropylhydroxysultaine, oleamidopropylhydroxysultaine, cocohydroxysultaine, laurylhydroxysultaine, and cocosultaine, alone or as mixtures.

The betaine-type amphoteric surfactant is preferably an alkylbetaine and an alkylamidoalkylbetaine, in particular cocobetaine and cocamidopropylbetaine.

Among the amidoaminecarboxylated derivatives, mention may be made of the products sold under the name Miranol, as described in U.S. Pat. Nos. 2,528,378 and 2,781,354 and classified in the CTFA dictionary, 3rd edition, 1982 (the disclosures of which are incorporated herein by reference), under the names Amphocarboxyglycinates and Amphocarboxypropionates, with the respective structures:

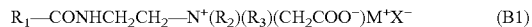

$$R_1\text{—CONHCH}_2\text{CH}_2\text{—N}^+(R_2)(R_3)(\text{CH}_2\text{COO}^-)\text{M}^+\text{X}^- \qquad (B1)$$

in which:
$R_1$ denotes an alkyl radical of an acid $R_1$—COOH present in hydrolysed coconut oil, a heptyl, nonyl or undecyl radical,
$R_2$ denotes a beta-hydroxyethyl group,
$R_3$ denotes a carboxymethyl group,
$M^+$ denotes a cationic ion derived from alkaline metals such as sodium; ammonium ion; or an ion derived from an organic amine;
$X^-$ denotes an organic or inorganic anionic ion such as halides, acetates, phosphates, nitrates, alkyl($C_1$-$C_4$)sulfates, alkyl($C_1$-$C_4$)— or alkyl($C_1$-$C_4$)aryl-sulfonates, particularly methylsulfate and ethylsulfate; or $M^+$ and $X^-$ are not present;

$$R_{1'}\text{—CONHCH}_2\text{CH}_2\text{—N(B)(C)} \qquad (B2)$$

in which:
$R_{1'}$ denotes an alkyl radical of an acid $R_{1'}$—COOH present in coconut oil or in hydrolysed linseed oil, an alkyl radical, such as a $C_7$, $C_9$, $C_{11}$ or $C_{13}$ alkyl radical, a $C_{17}$ alkyl radical and its iso-form, or an unsaturated $C_{17}$ radical,
B represents —$CH_2CH_2OX'$,
C represents —$(CH_2)_zY'$, with z=1 or 2,
X' denotes a —$CH_2$—COOH group, —$CH_2$—COOZ', —$CH_2CH_2$—COOH, —$CH_2CH_2$—COOZ' or a hydrogen atom, and
Y' denotes —COOH, —COOZ', —$CH_2$—CHOH—$SO_3Z'$, —$CH_2$—CHOH—$SO_3H$ radical or a —$CH_2$—CH(OH)—$SO_3$—Z' radical,
wherein Z' represents an ion of an alkaline or alkaline earth metal such as sodium, an ion derived from an organic amine or an ammonium ion;
and

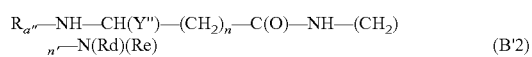

$$R_{a''}\text{—NH—CH(Y'')—(CH}_2)_n\text{—C(O)—NH—(CH}_2)_{n'}\text{—N(Rd)(Re)} \qquad (B'2)$$

in which:
Y'' denotes —C(O)OH, —C(O)OZ'', —$CH_2$—CH(OH)—$SO_3H$ or —$CH_2$—CH(OH)—$SO_3$—Z'', wherein
Z'' denotes a cationic ion derived from alkaline metal or alkaline-earth metals such as sodium, an ion derived from organic amine or an ammonium ion;
Rd and Re denote a $C_1$-$C_4$ alkyl or $C_1$-$C_4$ hydroxyalkyl radical;
$R_{a''}$ denotes a $C_{10}$-$C_{30}$ group alkyl or alkenyl group from an acid, and
n and n' independently denote an integer from 1 to 3.

It is preferable that the amphoteric surfactant with formula B1 and B2 be selected from ($C_8$-$C_{24}$)-alkyl amphomonoacetates, ($C_8$-$C_{24}$)alkyl amphodiacetates, ($C_8$-$C_{24}$)alkyl amphomonopropionates, and ($C_8$-$C_{24}$)alkyl amphodipropionates These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphopropionate, Disodium Caprylamphodipropionate, Disodium Capryloamphodipropionate, Lauroamphodipropionic acid and Cocoamphodipropionic acid.

By way of example, mention may be made of the cocoamphodiacetate sold under the trade name Miranol® $C_2M$ concentrate by the company Rhodia Chimie.

Among compounds of formula (B'2) mention may be made of sodium diethylaminopropyl cocoaspartamide (CTFA) marketed by CHIMEX under the denomination CHIMEXANE HB.

(iii) Cationic Surfactants

The composition may comprise at least one cationic surfactant. Two or more cationic surfactants may be used in combination.

The cationic surfactant may be selected from the group consisting of optionally polyoxyalkylenated, primary, secondary or tertiary fatty amine salts, quaternary ammonium salts, and mixtures thereof.

Examples of quaternary ammonium salts that may be mentioned include, but are not limited to:
those of general formula (B3) below:

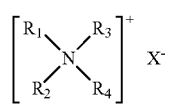

(B3)

wherein
$R_1$, $R_2$, $R_3$, and $R_4$, which may be identical or different, are chosen from linear and branched aliphatic radicals including from 1 to 30 carbon atoms and optionally including heteroatoms such as oxygen, nitrogen, sulfur and halogens. The aliphatic radicals may be chosen, for example, from alkyl, alkoxy, $C_2$-$C_6$ polyoxyalkylene, alkylamide, ($C_{12}$-$C_{22}$)alkylamido($C_2$-$C_6$)alkyl, ($C_{12}$-$C_{22}$)alkylacetate and hydroxyalkyl radicals; and aromatic radicals such as aryl and alkylaryl; and X" is chosen from halides, phosphates, acetates, lactates, ($C_2$-$C_6$) alkyl sulfates and alkyl- or alkylarylsulfonates; quaternary ammonium salts of imidazoline, for instance those of formula (B4) below:

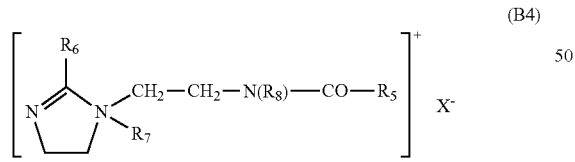

(B4)

wherein:
$R_5$ is chosen from alkenyl and alkyl radicals including from 8 to 30 carbon atoms, for example fatty acid derivatives of tallow or of coconut;
$R_6$ is chosen from hydrogen, $C_1$-$C_4$ alkyl radicals, and alkenyl and alkyl radicals including from 8 to 30 carbon atoms;
$R_7$ is chosen from $C_1$-$C_4$ alkyl radicals;
$R_8$ is chosen from hydrogen and $C_1$-$C_4$ alkyl radicals; and
$X^-$ is chosen from halides, phosphates, acetates, lactates, alkyl sulfates, alkyl sulfonates, and alkylaryl sulfonates. In one embodiment, $R_5$ and $R_6$ are, for example, a mixture of radicals chosen from alkenyl and alkyl radicals including from 12 to 21 carbon atoms, such as fatty acid derivatives of tallow, $R_7$ is methyl and $R_8$ is hydrogen. Examples of such products include, but are not limited to, Quaternium-27 (CTFA 1997) and Quaternium-83 (CTFA 1997), which are sold under the names "Rewoquat®" W75, W90, W75PG and W75HPG by the company Witco;
di or tri quaternary ammonium salts of formula (B5):

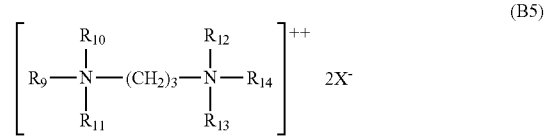

(B5)

wherein:
$R_9$ is chosen from aliphatic radicals including from 16 to 30 carbon atoms;
$R_{10}$ is chosen from hydrogen or alkyl radicals including from 1 to 4 carbon atoms or a group —$(CH_2)_3$ $(R_{16a})(R_{17a})(R_{18a})N^+X$—;
$R_{11}$, $R_{12}$, $R_{13}$, $R_{14}$, $R_{16a}$, $R_{17a}$, and $R_{18a}$, which may be identical or different, are chosen from hydrogen and alkyl radicals including from 1 to 4 carbon atoms; and
$X^-$ is chosen from halides, acetates, phosphates, nitrates, ethyl sulfates, and methyl sulfates.

An example of one such diquaternary ammonium salt is FINQUAT CTP of FINETEX (Quaternium-89) or FINQUAT CT (Quaternium-75);
and
quaternary ammonium salts including at least one ester function, such as those of formula (B6) below:

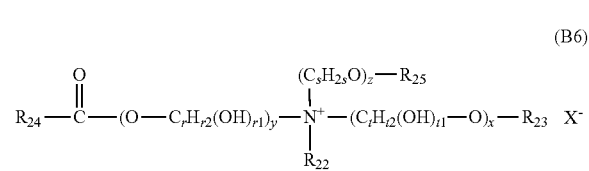

(B6)

wherein:
$R_{22}$ is chosen from $C_1$-$C_6$ alkyl radicals and $C_1$-$C_6$ hydroxyalkyl and dihydroxyalkyl radicals; $R_{23}$ is chosen from:
the radical below:

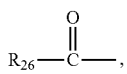

linear and branched, saturated and unsaturated $C_1$-$C_{22}$ hydrocarbon-based radicals $R_{27}$, and hydrogen,
$R_{25}$ is chosen from:
the radical below:

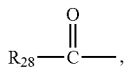

linear and branched, saturated and unsaturated $C_1$-$C_6$ hydrocarbon-based radicals $R_{29}$, and hydrogen,
$R_{24}$, $R_{26}$, and $R_{28}$, which may be identical or different, are chosen from linear and branched, saturated and unsaturated, $C_7$-$C_{21}$, hydrocarbon-based radicals;

r, s, and t, which may be identical or different, are chosen from integers ranging from 2 to 6; each of r1 and t1, which may be identical or different, is 0 or 1, and r2+r1=2r and t1+2t=2t;

y is chosen from integers ranging from 1 to 10;

x and z, which may be identical or different, are chosen from integers ranging from 0 to 10;

$X^-$ is chosen from simple and complex, organic and inorganic anions; with the proviso that the sum x+y+z ranges from 1 to 15, that when x is 0, $R_{23}$ denotes $R_{27}$, and that when z is 0, $R_{25}$ denotes $R_{29}$. $R_{22}$ may be chosen from linear and branched alkyl radicals. In one embodiment, $R_{22}$ is chosen from linear alkyl radicals. In another embodiment, $R_{22}$ is chosen from methyl, ethyl, hydroxyethyl, and dihydroxypropyl radicals, for example methyl and ethyl radicals. In one embodiment, the sum x+y+z ranges from 1 to 10. When $R_{23}$ is a hydrocarbon-based radical $R_{27}$, it may be long and include from 12 to 22 carbon atoms, or short and include from 1 to 3 carbon atoms. When $R_{25}$ is a hydrocarbon-based radical $R_{29}$, it may include, for example, from 1 to 3 carbon atoms. By way of a non-limiting example, in one embodiment, $R_{24}$, $R_{26}$, and $R_{28}$, which may be identical or different, are chosen from linear and branched, saturated and unsaturated, $C_{11}$-$C_{21}$ hydrocarbon-based radicals, for example from linear and branched, saturated and unsaturated $C_{11}$-$C_{21}$ alkyl and alkenyl radicals. In another embodiment, x and z, which may be identical or different, are 0 or 1. In one embodiment, y is equal to 1. In another embodiment, r, s and t, which may be identical or different, are equal to 2 or 3, for example equal to 2. The anion $X^-$ may be chosen from, for example, halides, such as chloride, bromide, and iodide; and $C_1$-$C_4$ alkyl sulfates, such as methyl sulfate. However, methanesulfonate, phosphate, nitrate, tosylate, an anion derived from an organic acid, such as acetate and lactate, and any other anion that is compatible with the ammonium including an ester function, are other non-limiting examples of anions that may be used according to the present invention. In one embodiment, the anion $X^-$ is chosen from chloride and methyl sulfate.

In another embodiment, the ammonium salts of formula (B6) may be used, wherein:

$R_{22}$ is chosen from methyl and ethyl radicals, x and y are equal to 1;

z is equal to 0 or 1;

r, s and t are equal to 2;

$R_{23}$ is chosen from:

the radical below:

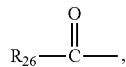

methyl, ethyl, and $C_{14}$-$C_{22}$ hydrocarbon-based radicals, hydrogen;

$R_{25}$ is chosen from:

the radical below:

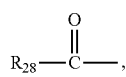

and hydrogen;

$R_{24}$, $R_{26}$, and $R_{28}$, which may be identical or different, are chosen from linear and branched, saturated and unsaturated, $C_{13}$-$C_{17}$ hydrocarbon-based radicals, for example from linear and branched, saturated and unsaturated, $C_{13}$-$C_{17}$ alkyl and alkenyl radicals.

In one embodiment, the hydrocarbon-based radicals are linear.

Non-limiting examples of compounds of formula (B6) that may be mentioned include salts, for example chloride and methyl sulfate, of diacyloxyethyl-dimethylammonium, of diacyloxyethyl-hydroxyethyl-methylammonium, of monoacyloxyethyl-dihydroxyethyl-methylammonium, of triacyloxyethyl-methylammonium, of monoacyloxyethyl-hydroxyethyl-dimethyl-ammonium, and mixtures thereof. In one embodiment, the acyl radicals may include from 14 to 18 carbon atoms, and may be derived, for example, from a plant oil, for instance palm oil and sunflower oil. When the compound includes several acyl radicals, these radicals may be identical or different.

These products may be obtained, for example, by direct esterification of optionally oxyalkylenated triethanolamine, triisopropanolamine, alkyldiethanolamine or alkyldiisopropanolamine onto fatty acids or onto mixtures of fatty acids of plant or animal origin, or by transesterification of the methyl esters thereof. This esterification may be followed by a quaternization using an alkylating agent chosen from alkyl halides, for example methyl and ethyl halides; dialkyl sulfates, for example dimethyl and diethyl sulfates; methyl methanesulfonate; methyl para-toluenesulfonate; glycol chlorohydrin; and glycerol chlorohydrin.

Such compounds are sold, for example, under the names Dehyquart® by the company Cognis, Stepanquat® by the company Stepan, Noxamium® by the company Ceca, and "Rewoquat® WE 18" by the company Rewo-Goldschmidt.

Other non-limiting examples of ammonium salts that may be used in the composition according to the present invention include the ammonium salts including at least one ester function described in U.S. Pat. Nos. 4,874,554 and 4,137,180.

Among the quaternary ammonium salts mentioned above, those that may be used in the composition according to the present invention include, but are not limited to, those corresponding to formula (I), for example tetraalkylammonium chlorides, for instance dialkyldimethylammonium and alkyltrimethylammonium chlorides in which the alkyl radical includes from about 12 to 22 carbon atoms, such as behenyltrimethylammonium, distearyldimethylammonium, cetyltrimethylammonium and benzyldimethylstearylammonium chloride; palmitylamidopropyltrimethylammonium chloride; and stearamidopropyldimethyl(myristyl acetate) ammonium chloride, sold under the name "Ceraphyl® 70" by the company Van Dyk.

According to one embodiment, the cationic surfactant that may be used in the composition according to the present invention is chosen from behenyltrimethylammonium chloride, cetyltrimethylammonium chloride, Quaternium-83, Quaternium-87, Quaternium-22, behenylamidopropyl-2,3-dihydroxypropyldimethylammonium chloride, palmitylamidopropyltrimethylammonium chloride, and stearamidopropyldimethylamine.

(iv) Nonionic Surfactants

The composition comprises at least one nonionic surfactant. Two or more nonionic surfactants may be used in combination.

The nonionic surfactants are compounds well known in themselves (see, e.g., in this regard, "Handbook of Surfactants" by M. R. Porter, Blackie & Son publishers (Glasgow and London), 1991, pp. 116-178). Thus, they can, for example, be chosen from alcohols, alpha-diols, alkylphenols and esters of fatty acids, these compounds being ethoxylated, propoxylated or glycerolated and having at least one fatty chain comprising, for example, from 8 to 30 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils of plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives; amine oxides such as ($C_{10}$-$C_{14}$)alkylamine oxides or N—($C_{10}$-$C_{14}$)acylaminopropylmorpholine oxides; silicone surfactants; and mixtures thereof.

The nonionic surfactants may preferably be chosen from monooxyalkylenated, polyoxyalkylenated, monoglycerolated or polyglycerolated nonionic surfactants. The oxyalkylene units are more particularly oxyethylene or oxypropylene units, or a combination thereof, and are preferably oxyethylene units.

Examples of monooxyalkylenated or polyoxyalkylenated nonionic surfactants that may be mentioned include:
monooxyalkylenated or polyoxyalkylenated ($C_8$-$C_{24}$)alkylphenols,
saturated or unsaturated, linear or branched, monooxyalkylenated or polyoxyalkylenated $C_8$-$C_{30}$ alcohols,
saturated or unsaturated, linear or branched, monooxyalkylenated or polyoxyalkylenated $C_8$-$C_{30}$ amides,
esters of saturated or unsaturated, linear or branched, $C_8$-$C_{30}$ acids and of polyalkylene glycols,
monooxyalkylenated or polyoxyalkylenated esters of saturated or unsaturated, linear or branched, $C_8$-$C_{30}$ acids and of sorbitol,
saturated or unsaturated, monooxyalkylenated or polyoxyalkylenated plant oils, condensates of ethylene oxide and/or of propylene oxide, inter alia, alone or as mixtures.

The surfactants preferably contain a number of moles of ethylene oxide and/or of propylene oxide of between 1 and 100 and most preferably between 2 and 50. According to one of the embodiments of the present invention, the polyoxyalkylenated nonionic surfactants are chosen from polyoxyethylenated fatty alcohols (polyethylene glycol ether of fatty alcohol) and polyoxyethylenated fatty esters (polyethylene glycol ester of fatty acid).

Examples of polyoxyethylenated saturated fatty alcohols (or $C_8$-$C_{30}$ alcohols) that may be mentioned include the adducts of ethylene oxide with lauryl alcohol, especially those containing from 2 to 50 oxyethylene units and more particularly those containing from 10 to 12 oxyethylene units (Laureth-10 to Laureth-12, as the CTFA names); the adducts of ethylene oxide with behenyl alcohol, especially those containing from 2 to 50 oxyethylene units (Beheneth-9 to Beheneth-50, as the CTFA names); the adducts of ethylene oxide with cetearyl alcohol (mixture of cetyl alcohol and stearyl alcohol), especially those containing from 2 to 30 oxyethylene units (Ceteareth-10 to Ceteareth-30, as the CTFA names); the adducts of ethylene oxide with cetyl alcohol, especially those containing from 2 to 30 oxyethylene units (Ceteth-10 to Ceteth-30, as the CTFA names); the adducts of ethylene oxide with stearyl alcohol, especially those containing from 2 to 30 oxyethylene units (Steareth-2 to Steareth-30, as the CTFA names); the adducts of ethylene oxide with isostearyl alcohol, especially those containing from 2 to 50 oxyethylene units (Isosteareth-2 to Isosteareth-50, as the CTFA names); and mixtures thereof.

Examples of polyoxyethylenated unsaturated fatty alcohol (or $C_8$-$C_{30}$ alcohols) that may be mentioned include the adducts of ethylene oxide with oleyl alcohol, especially those containing from 2 to 50 oxyethylene units and more particularly those containing from 10 to 40 oxyethylene units (Oleth-10 to Oleth-40, as the CTFA names); and mixtures thereof.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

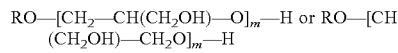

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the present invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is preferable to use the $C_8$/$C_{10}$ alcohol containing 1 mol of glycerol, the $C_{10}$/$C_{12}$ alcohol containing 1 mol of glycerol and the $C_{12}$ alcohol containing 1.5 mol of glycerol.

The monoglycerolated or polyglycerolated $C_5$-$C_{40}$ fatty esters may correspond to the following formula:

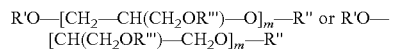

in which each of R', R" and R'" independently represents a hydrogen atom, or a linear or branched $C_8$-$C_{40}$ and preferably $C_8$-$C_{30}$ alkyl-CO— or alkenyl-CO-radical, with the proviso that at least one of R', R" and R'" is not a hydrogen atom, and m represents a number ranging from 1 to 30 and preferably from 1.5 to 10.

Examples of polyoxyethylenated fatty esters that may be mentioned include the adducts of ethylene oxide with esters of lauric acid, palmitic acid, stearic acid or behenic acid, and mixtures thereof, especially those containing from 9 to 100 oxyethylene units, such as PEG-9 to PEG-50 laurate (CTFA names: PEG-9 laurate to PEG-50 laurate); PEG-9 to PEG-50 palmitate (CTFA names: PEG-9 palmitate to PEG-50 palmitate); PEG-9 to PEG-50 stearate (CTFA names: PEG-9 stearate to PEG-50 stearate); PEG-9 to PEG-50 palmitostearate; PEG-9 to PEG-50 behenate (CTFA names: PEG-9 behenate to PEG-50 behenate); polyethylene glycol 100 EO monostearate (CTFA name: PEG-100 stearate); and mixtures thereof.

According to one of the embodiments of the present invention, the nonionic surfactant may be selected from esters of polyols with fatty acids with a saturated or unsaturated chain containing for example from 8 to 24 carbon atoms, preferably 12 to 22 carbon atoms, and polyoxyalkylenated derivatives thereof, preferably containing from 10 to 200, and more preferably from 10 to 100 oxyalkylene units, such as glyceryl esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sorbitol esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sugar (sucrose, maltose, glucose, fructose, and/or alkylglycose) esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; ethers of fatty alcohols; ethers of sugar and a $C_8$-$C_{24}$, preferably $C_{12}$-$C_{22}$, fatty alcohol or alcohols; and mixtures thereof.

As glyceryl esters of fatty acids, glyceryl stearate (glyceryl mono-, di- and/or tristearate) (CTFA name: glyceryl stearate), glyceryl laurate or glyceryl ricinoleate and mixtures thereof can be cited, and as polyoxyalkylenated derivatives thereof, mono-, di- or triester of fatty acids with a polyoxyalkylenated glycerol (mono-, di- or triester of fatty acids with a polyalkylene glycol ether of glycerol), preferably polyoxyethylenated glyceryl stearate (mono-, di- and/or tristearate), such as PEG-20 glyceryl stearate (mono-, di- and/or tristearate) can be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEGIN by Goldschmidt (CTFA name: glyceryl stearate SE), can also be used.

The sorbitol esters of $C_8$-$C_{24}$ fatty acids and polyoxyalkylenated derivatives thereof can be selected from sorbitan palmitate, sorbitan isostearate, sorbitan trioleate and esters of fatty acids and alkoxylated sorbitan containing for example from 20 to 100 EO, such as for example sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: polysorbate 65), sold by the company ICI under the name Tween 65, polyethylene sorbitan trioleate (polysorbate 85) or the compounds marketed under the trade names Tween 20 or Tween 60 by Uniqema.

As esters of fatty acids and glucose or alkylglucose, glucose palmitate, alkylglucose sesquistearates such as methylglucose sesquistearate, alkylglucose palmitates such as methylglucose or ethylglucose palmitate, methylglucoside fatty esters, the diester of methylglucoside and oleic acid (CTFA name: Methyl glucose dioleate), the mixed ester of methylglucoside and the mixture of oleic acid/hydroxystearic acid (CTFA name: Methyl glucose dioleate/hydroxystearate), the ester of methylglucoside and isostearic acid (CTFA name: Methyl glucose isostearate), the ester of methylglucoside and lauric acid (CTFA name: Methyl glucose laurate), the mixture of monoester and diester of methylglucoside and isostearic acid (CTFA name: Methyl glucose sesqui-isostearate), the mixture of monoester and diester of methylglucoside and stearic acid (CTFA name: Methyl glucose sesquistearate) and in particular the product marketed under the name Glucate SS by AMERCHOL, and mixtures thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (CTFA name: PEG-20 methyl glucose distearate) such as the product marketed under the name Glucam E-20 distearate by AMERCHOL, the polyethylene glycol ether of the mixture of monoester and diester of methyl-glucose and stearic acid with about 20 moles of ethylene oxide (CTFA name: PEG-20 methyl glucose sesquistearate) and in particular the product marketed under the name Glucamate SSE-20 by AMERCHOL and that marketed under the name Grillocose PSE-20 by GOLDSCHMIDT, and mixtures thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLANTAREN 2000 by Henkel, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by Henkel, coco-glucoside such as the product marketed under the name PLANTACARE 818/UP by Henkel, cetostearyl glucoside possibly mixed with cetostearyl alcohol, marketed for example under the name MONTANOV 68 by Seppic, under the name TEGO-CARE CG90 by Goldschmidt and under the name EMULGADE KE3302 by Henkel, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and mixtures thereof can in particular be cited.

Mixtures of glycerides of alkoxylated plant oils such as mixtures of ethoxylated (200 EO) palm and copra (7 EO) glycerides can also be cited.

The nonionic surfactant according to the present invention preferably contains alkenyl or a branched $C_{12}$-$C_{22}$ acyl chain such as an oleyl or isostearyl group. More preferably, the nonionic surfactant according to the present invention is PEG-20 glyceryl triisostearate.

According to one of the embodiments of the present invention, the nonionic surfactant may be selected from copolymers of ethylene oxide and of propylene oxide, in particular copolymers of the following formula:

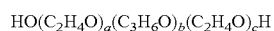

in which a, b and c are integers such that a+c ranges from 2 to 100 and b ranges from 14 to 60, and mixtures thereof.

According to one of the embodiments of the present invention, the nonionic surfactant may be selected from silicone surfactants. Non-limiting mention may be made of those disclosed in documents U.S. Pat. Nos. 5,364,633 and 5,411,744.

The silicone surfactant may preferably be a compound of formula (I):

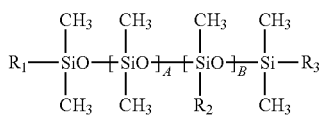 (I)

in which:
R$_1$, R$_2$ and R$_3$, independently of each other, represent a C$_1$-C$_6$ alkyl radical or a radical —(CH$_2$)$_x$—(OCH$_2$CH$_2$)$_y$—(OCH$_2$CH$_2$)$_z$—OR$_4$, at least one radical R$_1$, R$_2$ or R$_3$ not being an alkyl radical; R$_4$ being a hydrogen, an alkyl radical or an acyl radical;
A is an integer ranging from 0 to 200;
B is an integer ranging from 0 to 50; with the proviso that A and B are not simultaneously equal to zero;
x is an integer ranging from 1 to 6;
y is an integer ranging from 1 to 30;
z is an integer ranging from 0 to 5.

According to one preferred embodiment of the present invention, in the compound of formula (I), the alkyl radical is a methyl radical, x is an integer ranging from 2 to 6 and y is an integer ranging from 4 to 30.

As examples of silicone surfactants of formula (I), mention may be made of the compounds of formula (II):

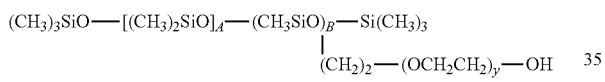 (II)

in which A is an integer ranging from 20 to 105, B is an integer ranging from 2 to 10 and y is an integer ranging from 10 to 20.

As examples of silicone surfactants of formula (I), mention may also be made of the compounds of formula (III):

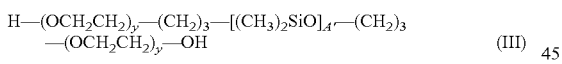 (III)

in which A' and y are integers ranging from 10 to 20.

Compounds of the present invention which may be used are those sold by the company Dow Corning under the names DC 5329, DC 7439-146, DC 2-5695 and Q4-3667. The compounds DC 5329, DC 7439-146 and DC 2-5695 are compounds of formula (II) in which, respectively, A is 22, B is 2 and y is 12; A is 103, B is 10 and y is 12; and A is 27, B is 3 and y is 12.

The compound Q4-3667 is a compound of formula (III) in which A is 15 and y is 13.

(Conditioning Agent)

The composition according to the present invention may further comprise at least one conditioning agent. Two or more conditioning agents may be used in combination. Thus, a single type of conditioning agent or a combination of different types of conditioning agents may be used.

The conditioning agent can provide keratin fibers such as hair with conditioning effects.

It is preferable that the conditioning agent be selected from cationic polymers.

The composition according to the present invention may comprise at least one cationic polymer. A single type of cationic polymer may be used, but two or more different types of cationic polymers may be used in combination.

It should be noted that, for the purposes of the present invention, the term "cationic polymer" denotes any polymer containing cationic groups and/or groups that may be ionized into cationic groups.

Such polymers may be chosen from those already known per se as improving the cosmetic properties of the hair, i.e., especially those described in patent application EP-A-337 354 and in French patents FR-2 270 846, 2 383 660, 2 598 611, 2 470 596 and 2 519 863.

The cationic polymers that are preferred are chosen from those containing units comprising primary, secondary, tertiary and/or quaternary amine groups, which may either form part of the main polymer chain or may be borne by a side substituent directly attached thereto.

The cationic polymers used generally have a number-average molecular mass of between approximately 500 and approximately 5×10$^6$ and preferably between approximately 10$^3$ and approximately 3×10$^6$.

Among the cationic polymers that may be mentioned more particularly are polymers of the polyamine, polyamino amide and polyquaternary ammonium type.

These are known products. They are described in particular in French patents 2 505 348 and 2 542 997. Among the said polymers, mention may be made of the following.

(1) homopolymers or copolymers derived from acrylic or methacrylic esters or amides and comprising at least one of the units of formula (I), (II), (III) or (IV) below:

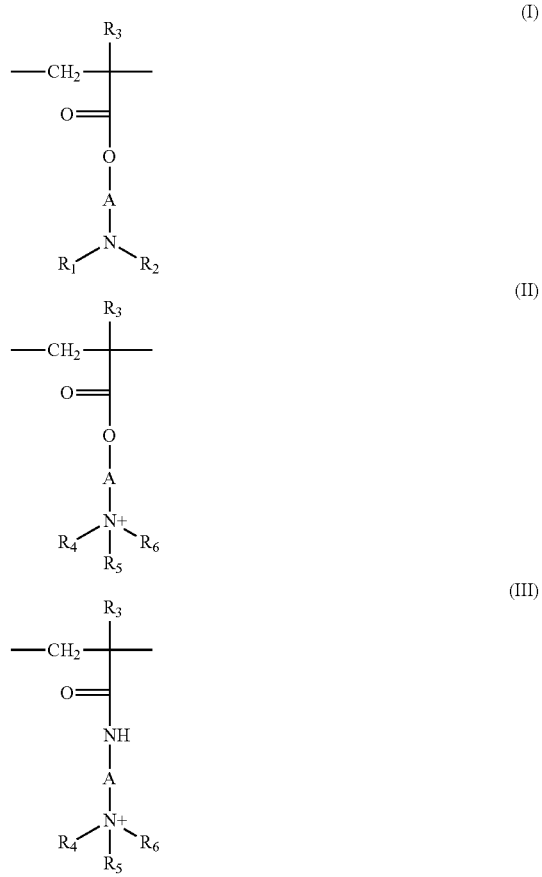

-continued

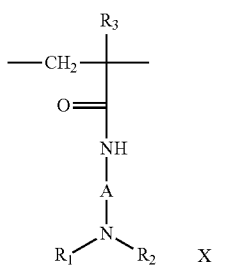
(IV)

in which
$R_3$, which may be identical or different, denote a hydrogen atom or a $CH_3$ radical;
A, which may be identical or different, represent a linear or branched alkyl group of 1 to 6 carbon atoms, preferably 2 or 3 carbon atoms, or a hydroxyalkyl group of 1 to 4 carbon atoms;
$R_4$, $R_5$ and $R_6$, which may be identical or different, represent an alkyl group containing from 1 to 18 carbon atoms or a benzyl radical and preferably an alkyl group containing from 1 to 6 carbon atoms;
$R_1$ and $R_2$, which may be identical or different, represent hydrogen or an alkyl group containing from 1 to 6 carbon atoms, and preferably methyl or ethyl; and
X denotes an anion derived from an inorganic or organic acid, such as a methosulfate anion or a halide such as chloride or bromide.

The polymers of family (1) can also contain one or more units derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinyl-caprolactam, and vinyl esters.

Thus, among these polymers of family (1), mention may be made of:
copolymers of acrylamide and of dimethylaminoethyl methacrylate quaternized with dimethyl sulfate or with a dimethyl halide, such as the product sold under the name Hercofloc by the company Hercules,
the copolymers of acrylamide and of methacryloyloxyethyltrimethylammonium chloride described, for example, in patent application EP-A-080 976 and sold under the name Bina Quat P 100 by the company BASF,
the copolymer of acrylamide and of methacryloyloxyethyltrimethylammonium methosulfate sold under the name Reten by the company Hercules,
quaternized or non-quaternized vinylpyrrolidone/dialkylaminoalkyl acrylate or methacrylate copolymers, such as the products sold under the name "Gafquat" by the company ISP, for instance "Gafquat 734" or "Gafquat 755", or alternatively the products known as "Copolymer 845, 958 and 937". These polymers are described in detail in French patents 2 077 143 and 2 393 573,
dimethylaminoethyl methacrylate/vinylcaprolactam/vinylpyrrolidone terpolymers, such as the product sold under the name Gaffix VC 713 by the company ISP, and
vinylpyrrolidone/methacrylamidopropyldimethylamine copolymers sold in particular under the name Styleze CC 10 by ISP, and quaternized vinylpyrrolidone/dimethylaminopropyl methacrylamide copolymers such as the product sold under the name "Gafquat HS 100" by the company ISP.

(2) The cellulose ether derivatives comprising quaternary ammonium groups, which are described in French patent 1 492 597, and in particular the polymers sold under the names "JR" (JR 400, JR 125, JR 30M) or "LR" (LR 400, LR 30M) by the company Amerchol. These polymers are also defined in the CTFA dictionary as hydroxyethylcellulose quaternary ammoniums that have reacted with an epoxide substituted with a trimethylammonium group.

(3) Cationic cellulose derivatives such as the copolymers of cellulose or cellulose derivatives grafted with a water-soluble quaternary ammonium monomer, described especially in U.S. Pat. No. 4,131,576, such as hydroxyalkylcelluloses, for instance hydroxymethyl-, hydroxyethyl- or hydroxypropylcelluloses grafted especially with a methacryloylethyl-trimethylammonium, methacrylamidopropyltrimethylammonium or dimethyldiallylammonium salt.

The commercial products corresponding to this definition are more particularly the products sold under the name Celquat L 200 and Celquat H 100 by the company Akzo Nobel.

(4) The cationic guar gums described more particularly in U.S. Pat. Nos. 3,589,578 and 4,031,307, such as guar gums containing trialkylammonium cationic groups. Use is made, for example, of guar gums modified with a salt (e.g., chloride) of 2,3-epoxypropyltrimethylammonium. Mention may be made of guar hydroxypropyltrimonium chloride and hydroxypropyl guar hydroxypropyl trimonium chloride, such as those sold especially under the trade names Jaguar C13S, Jaguar C14S, Jaguar C17 and Jaguar C162 by the company Solvay.

(5) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, and also the oxidation and/or quaternization products of these polymers. Such polymers are described, in particular, in French patents 2 162 025 and 2 280 361.

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.

(7) Cyclopolymers of alkyldiallylamine or of dialkyldiallylammonium, such as the homopolymers or copolymers containing, as a main constituent of the chain, units corresponding to formula (V) or (VI):

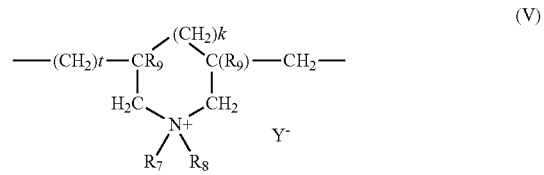
(V)

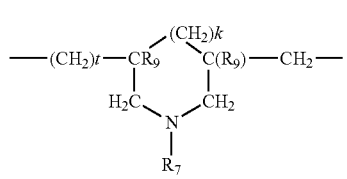

(VI)

in which formulae
k and t are equal to 0 or 1, the sum k+t being equal to 1; $R_9$ denotes a hydrogen atom or a methyl radical; $R_7$ and $R_8$, independently of each other, denote an alkyl group having from 1 to 6 carbon atoms, a hydroxyalkyl group in which the alkyl group preferably has 1 to 5 carbon atoms, a lower ($C_1$-$C_4$) amidoalkyl group, or $R_7$ and $R_8$ can denote, together with the nitrogen atom to which they are attached, heterocyclic groups such as piperidyl or morpholinyl; $R_7$ and $R_8$, independently of each other, preferably denote an alkyl group having from 1 to 4 carbon atoms; and $Y^-$ is an anion such as bromide, chloride, acetate, borate, citrate, tartrate, bisulfate, bisulfite, sulfate or phosphate. These polymers are described in particular in French patent 2 080 759 and in its Certificate of Addition 2 190 406.

Among the polymers defined above, mention may be made more particularly of the dimethyldiallylammonium chloride homopolymer sold under the name "Merquat 100" by the company Nalco (and its homologues of low weight-average molecular mass) and the copolymers of diallyldimethylammonium chloride and of acrylamide, sold under the name "Merquat 550".

(8) The quaternary diammonium polymer containing repeating units corresponding to the formula:

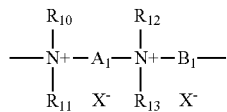

(VII)

in which formula (VII):
$R_{10}$, $R_{11}$, $R_{12}$ and $R_{13}$, which may be identical or different, represent aliphatic, alicyclic or arylaliphatic radicals containing from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;
$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and
$X^-$ denotes an anion derived from an inorganic or organic acid;
$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —$(CH_2)_n$—CO-D-OC—$(CH_2)_n$— in which D denotes:
i) a glycol residue of formula: —O—Z—O—, where Z denotes a linear or branched hydrocarbon-based radical or a group corresponding to one of the following formulae:
—($CH_2$—$CH_2$—O)$_x$—$CH_2$—$CH_2$—; and
—[$CH_2$—CH($CH_3$)—O]$_y$—$CH_2$—CH($CH_3$)—
where x and y denote an integer from 1 to 4, representing a defined and unique degree of polymerization or any number from 1 to 4 representing an average degree of polymerization;
ii) a bis-secondary diamine residue such as a piperazine derivative;
iii) a bis-primary diamine residue of formula —NH—Y—NH—, where Y denotes a linear or branched hydrocarbon-based radical, or alternatively the divalent radical —$CH_2$—$CH_2$—S—S—$CH_2$—$CH_2$—; or
iv) a ureylene group of formula —NH—CO—NH—.

Preferably, $X^-$ is an anion such as chloride or bromide.
These polymers generally have a number-average molecular mass of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to the following formula (VIII):

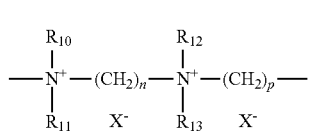

(VIII)

in which
$R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 20 approximately, and $X^-$ is an anion derived from a mineral or organic acid.

One particularly preferred compound of formula (VIII) is that for which $R_{10}$, $R_{11}$ $R_{12}$ and $R_{13}$ represent a methyl group, n=3, p=6 and X=Cl, which is called Hexadimethrine chloride according to the INCI(CTFA) nomenclature.

(9) Polyamines such as Polyquart H sold by Cognis, which is given under the reference name "Polyethylene glycol (15) tallow polyamine" in the CTFA dictionary.

(10) Crosslinked methacryloyloxy($C_1$-$C_4$)alkyltri($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethylammonium chloride copolymer (20/80 by weight) in the form of a dispersion containing 50% by weight of the said copolymer in mineral oil can be used more particularly. This dispersion is sold under the name "Salcare® SC 92" by the company BASF. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

(11) Other cationic polymers which can be used in the context of the present invention are polyalkyleneimines, in particular polyethyleneimines, polymers containing vinylpyridine or vinylpyridinium units, condensates of polyamines and of epichlorohydrin, quaternary polyureylenes and chitin derivatives.

It is preferable that the cationic polymer be a polyquaternium polymer or a polymeric quaternary ammonium salt.

Polymeric quaternary ammonium salts are cationic polymers comprising at least one quaternized nitrogen atom. Mention may in particular be made, as polymeric quaternary ammonium salts, of the Polyquaternium products (CTFA name), which contribute mainly to the quality of foam and feeling of the skin after use, in particular the feeling of the skin after use. These polymers can preferably be chosen from the following polymers:

Polyquaternium-5, such as the product Merquat 5 sold by Nalco;
Polyquaternium-6, such as the product Salcare SC 30 sold by BASF and the product Merquat 100 sold by Nalco;
Polyquaternium-7, such as the products Merquat S, Merquat 2200, Merquat 7SPR, and Merquat 550 sold by Nalco and the product Salcare SC 10 sold by BASF;
Polyquaternium-10, such as the product Polymer JR400 sold by Amerchol;
Polyquaternium-11, such as the products Gafquat 755, Gafquat 755N and Gafquat 734 sold by ISP;
Polyquaternium-15, such as the product Rohagit KF 720 F sold by Röhm;
Polyquaternium-16, such as the products Luviquat FC905, Luviquat FC370, Luviquat HM552 and Luviquat FC550 sold by BASF;
Polyquaternium-28, such as the product Styleze CC10 sold by ISP;
Polyquaternium-44, such as the product Luviquat Care sold by BASF;
Polyquaternium-46, such as the product Luviquat Hold sold by BASF;
Polyquaternium-47, such as the product Merquat 2001 sold by Nalco; and
Polyquaternium-67, such as the product Softcat SL-5, SL-30, SL-60 and SL-100 sold by Amerchol.

Preferably, the cationic polymer is chosen from, Polyquaternium-10, Polyquaternium-47, Polyquaternium-67, hydroxypropyl guar hydroxypropyl trimonium chloride and their mixtures.

The amount of the conditioning agent(s) such as cationic polymer(s) is not limited, but the amount of the conditioning agent(s) may be from 0.01 to 10% by weight, preferably 0.05 to 5% by weight, and more preferably 0.1 to 1% by weight, relative to the total weight of the composition.

(Organic Acid Salt of Alkaline Earth Metal)

The composition according to the present invention may further comprise at least one organic acid salt of alkaline earth metal. Two or more such salts may be used in combination. Thus, a single type of such salt or a combination of different types of such salts may be used.

If a plurality of organic acid salts of alkaline earth metal are used, it is possible that the type of organic acid is different and/or the type of alkaline earth metal is different.

The alkaline earth metal may be selected from magnesium and calcium.

The type of the (d) organic acid is independent from the type of the organic acid forming the organic acid salt of alkaline earth metal. It is preferable that the (d) organic acid is different from the organic acid forming the organic acid salt of alkaline earth metal.

The organic acid may be selected from α-hydroxy acids.

The α-hydroxy acids may be represented by the following formula (I):

wherein
R1=H, —OH, —NH$_2$, —CH$_2$COOH or a linear or branched C$_{1-4}$ alkyl,
R$_2$=H, —COOH, —CHOH—COOH, —CF$_3$, —CH=CH$_2$, —NHCONH$_2$, a linear, branched or cyclic C$_{1-8}$ alkyl optionally substituted with a radical chosen from —OH, Cl, —NH$_2$, —COOH, —CF$_3$ and —SCH$_3$; a phenyl or benzyl optionally substituted with one —OH or —OCH$_3$ radical; or alternatively the radical

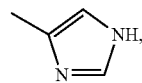

and
R$_1$ and R$_2$ may also together form an oxo radical (=O) or a cyclopropyl, cyclobutyl, hydroxycyclobutyl, cyclopentyl or cyclohexyl ring with the carbon atom that bears them, or alternatively the radical

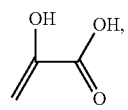

and
when R$_1$=H, R$_2$ may also represent a —(CHOH)$_2$CH$_2$OH or —(CHOH)$_3$CH$_2$OH radical, R=—OH or —NR3R4 with R3, R4=H or a linear or branched C$_{1-4}$ alkyl optionally substituted with one or two OH radicals, as well as stereoisomers, organic or mineral salts and solvates thereof.

The α-hydroxy acids may be selected from the following: glycolic acid, oxalic acid, lactic acid, 1-hydroxy-1-cyclopropanecarboxylic acid, 2-hydroxy-3-butenoic acid, 2-hydroxyisobutyric acid, 2-hydroxy-n-butyric acid, isoserine, glyceric acid, 2-hydroxy-3-methylbutyric acid, 2-hydroxy-2-methylbutyric acid, 2-hydroxyvaleric acid, 4-amino-2-hydroxybutyric acid, 1-hydroxycyclohexanecarboxylic acid, dihydroxyfumaric acid, citramalic acid, tartaric acid, citric acid, 2-hydroxy-4-(methylthio)butyric acid, mandelic acid, 2-hydroxy-3-methylvaleric acid, glyoxylurea, β-imidazole-lactic acid, 2-trifluoromethyl-2-hydroxypropionic acid, hexahydromandelic acid, 2-hydroxyoctanoic acid, arabic acid, 3-phenyllactic acid, hydroxyphenylglycine, 3-hydroxymandelic acid, 4-hydroxymandelic acid, 2-hydroxynonanoic acid, L-arginic acid, 3-methoxymandelic acid, 4-methoxymandelic acid, 3-(4-hydroxyphenyl)lactic acid, tartronic acid, β-chlorolactic acid, 1-cyclopentanol-1-carboxylic acid, 1,2-dihydroxycyclobutanecarboxylic acid, 2-ethyl-2-hydroxybutric acid, α-hydroxyisocaproic acid, α-hydroxycaproic acid, 2-hydroxy-3,3-dimethylbutyric acid, malic acid, hydroxytartronic acid, gluconic acid, lactamide, N-methyllactamide, N-ethyllactamide, N,N-dimethyllactamide, N-2-hydroxyethyllactamide, and stereoisomers, organic or mineral salts and solvates thereof.

It may be preferable that the α-hydroxy acid be selected from the group consisting of glycolic acid, oxalic acid, L-lactic acid, DL-lactic acid, D-lactic acid, malic acid, tartaric acid, DL-glyceric acid, arabic acid, gluconic acid, hydroxytartronic acid, lactamide, N-methyllactamide, N-ethyllactamide, and N-2-hydroxyethyllactamide.

It may be more preferable that α-hydroxy acid be selected from the group consisting of gluconic acid, glycolic acid, lactic acid, malic acid, citric acid, tartaric acid, and mandelic acid.

It may be even more preferable that the α-hydroxy acid be gluconic acid. If gluconate is used as the organic acid salt of alkaline earth metal, in particular Mg, the time period of the heating step (ii) in the process according to the present invention can be shortened. Although not bound by any theory, it is believed that this effect is based on catalytic effects of the alkaline earth metal gluconate such as magnesium gluconate.

The amount of the organic acid salt(s) of alkaline earth metal in the composition according to the present invention may be 0.001% by weight or more, preferably 0.01% by weight or more, and more preferably more than 0.1% by weight, relative to the total weight of the composition.

On the other hand, the amount of the organic acid salt(s) of alkaline earth metal in the composition according to the present invention may be 10% by weight or less, preferably 5% by weight or less, and more preferably 1% by weight or less, relative to the total weight of the composition.

The amount of the organic acid salt(s) of alkaline earth metal in the composition may be from 0.001 to 10% by weight, preferably from 0.01 to 5% by weight, and more preferably from more than 0.1% to 1% by weight, relative to the total weight of the composition.

(Other Ingredients)

The composition according to the present invention may also comprise at least one additional ingredient.

The amount of the additional ingredient(s) is not limited, but may be from 0.1 to 10% by weight relative to the total weight of the composition according to the present invention. The additional ingredient(s) may be selected from the group consisting of hydrophilic thickeners; anionic, nonionic or amphoteric polymers; peptides and derivatives thereof; protein hydrolyzates; swelling agents and penetrating agents; agents for combating hair loss; anti-dandruff agents; associative-type or not, natural or synthetic thickeners for oils; suspending agents; sequestering agents; opacifying agents; dyes; sunscreen agents; vitamins or provitamins; fragrances; preserving agents, stabilizers; and mixtures thereof.

Since the present invention does not perform reducing and oxidizing keratin fibers for reshaping the keratin fibers, the composition according to the present invention may be free from a reducing agent or an oxidizing agent which is conventionally used in, for example, permanent waving of keratin fibers such as hair.

However, if necessary, it may be possible for the composition according to the present invention to include a very small amount of a reducing agent or an oxidizing agent, in particular a reducing agent.

For example, the composition according to the present invention may comprise less than 2% by weight, preferably less than 1% by weight, and more preferably less than 0.1% by weight, of a reducing agent. It is most preferable that the composition according to the present invention include no reducing agent.

In any event, the composition according to the present invention can reduce the damage to the keratin fibers because the upper limit of the reducing agent in the composition according to the present invention is very low.

[Method and Use]

The present invention also relates to a method for enhancing reshaping efficiency of keratin fibers as a result of a reshaping process of the keratin fibers with a composition having a pH of 8.0 to 13.5, preferably from 8.5 to 12.0, and more preferably from 9.0 to 11.0, without reducing or oxidizing the keratin fibers, characterized by adding at least one diol selected from $C_{4-5}$ diols to the composition.

The present invention also relates to a use of at least one diol selected from $C_{4-5}$ diols in a composition having a pH of 8.0 to 13.5, preferably from 8.5 to 12.0, and more preferably from 9.0 to 11.0, wherein the composition is used for reshaping keratin fibers without reducing or oxidizing the keratin fibers, for enhancing reshaping efficiency of the keratin fibers.

The details of $C_{4-5}$ diols and the other details of the composition used in the method and use according to the present invention are the same as those explained in the section titled [Composition] above. Thus, the composition used in the method and use according to the present invention can be the same as the composition according to the present invention.

EXAMPLES

The present invention will be described in a more detailed manner by way of examples. However, these examples should not be construed as limiting the scope of the present invention.

Examples 1-2 and Comparative Examples 1-4

{Preparations}

The following compositions according to Examples 1 and 2 and Comparative Examples 1-4 shown in Table 1 were prepared by mixing the ingredients shown in Table 1. The numerical values for the amounts of the ingredients shown in Table 1 are all based on "% by weight" as active raw materials. The compositions according to Examples 1 and 2 and Comparative Examples 1-4 were in the form of a gel.

TABLE 1

|  | Ex 1 | Ex 2 | Comp. Ex. 1 | Comp. Ex. 2 | Comp. Ex. 3 | Comp. Ex. 4 |
| --- | --- | --- | --- | --- | --- | --- |
| KOH | 6.8 | 6.8 | 6.8 | 6.8 | 6.8 | 6.8 |
| Taurine | 15.4 | 15.4 | 15.4 | 15.4 | 15.4 | 15.4 |
| Butylene Glycol | 10 | — | — | — | — | — |
| Pentylene Glycol | — | 10 | — | — | — | — |
| Glycerin | — | — | — | 10 | — | — |
| Propylene Glycol | — | — | — | — | 10 | — |
| Hexylen Glycol | — | — | — | — | — | 10 |
| Hydroxyethylcellulose | 1.5 | 1.5 | 1.5 | 1.5 | 1.5 | 1.5 |

TABLE 1-continued

|  | Ex 1 | Ex 2 | Comp. Ex. 1 | Comp. Ex. 2 | Comp. Ex. 3 | Comp. Ex. 4 |
|---|---|---|---|---|---|---|
| Polyquaternitun-67 | 0.5 | 0.5 | 0.5 | 0.5 | 0.5 | 0.5 |
| Dimethicone | 0.2 | 0.2 | 0.2 | 0.2 | 0.2 | 0.2 |
| Water | qsp 100 | qsp 100 | qsp 100 | qsp 100 | qsp 100 | qsp 100 |
| pH | 10.7 | 10.7 | 10.7 | 10.7 | 10.7 | 10.7 |
| Curl Efficiency | Good | Good | Fair | Poor | Poor | Fair |
| Curl Number | Good | Good | Fair | Poor | Poor | Fair |

Evaluations 3 g of each composition was applied on 3 g of a pre-shampooed Chinese hair swatch, and the hair was wound onto a 18-mm perm rod and covered by a physical wrap of a plastic film, and then heated by a digital perm machine (ASIA perm machine) for 20 minutes at 90° C. After removing the physical wrap, the hair on rod was cooled at ambient temperature for 5 minutes and removed from the rod. The hair was then rinsed with tap water, the curl shape was aligned, and the hair was dried in an oven.

The curl efficiency and the curl number of the curled hair were evaluated as follows.
(Curl Efficiency)

The value of $(L_0-L)/L_0$ (wherein $L_0$ means the length of hair before curling and L means the length of hair after curling) was determined for each of the hair swatches by measuring the length of the hair before and after curling, and the determined value was evaluated in accordance with the following criteria.
Very Good: Equal to or more than 0.16
Good: Equal to or more than 0.13 and less than 0.16
Fair: Equal to or more than 0.11 and less than 0.13
Poor: Less than 0.11
The results are shown in Table 1
(Curl Number)

The number of curls was counted for each of the hair swatches, and evaluated in accordance with the following criteria.
Very Good: Equal to or more than 11
Good: Equal to or more than 9 and less than 11
Fair: Equal to or more than 7 and less than 9
Poor: Less than 7
The results are shown in Table 1.

Larger curl number and larger curl efficiency mean better curl performance.

As shown in Table 1, butylene glycol and pentylene glycol enhanced the curl performance, whereas glycerin and propylene glycol decreased the curl efficacy, and hexylene glycol did not enhance the performance.

Examples 3-5 and Comparative Example 5

{Preparations}

The following compositions according to Examples 3-4 and Comparative Example 5 shown in Table 2 were prepared by mixing the ingredients shown in Table 2. The numerical values for the amounts of the ingredients shown in Table 2 are all based on "% by weight" as active raw materials. The compositions according to Examples 3-5 and Comparative Example 5 were in the form of an emulsion.

TABLE 2

|  | Ex. 3 | Ex. 4 | Ex. 5 | Comp. Ex. 5 |
|---|---|---|---|---|
| NaOH | 2.4 | 2.4 | 2.4 | 2.4 |
| Monoethanolamine | 3.6 | 3.6 | 3.6 | 3.6 |
| Taurine | 8.7 | 8.7 | 8.7 | 8.7 |
| Magnesium Gluconate | 0.125 | 0.125 | 0.125 | 0.125 |
| Pentylene Glycol | 10 | 7.5 | 5 | — |
| Ethanol | — | 2.5 | 5 | — |
| Hydroxyethylcellulose | 1.5 | 1.5 | 1.5 | 1.5 |
| Polyquatemium-67 | 0.5 | 0.5 | 0.5 | 0.5 |
| Dimethicone | 0.2 | 0.2 | 0.2 | 0.2 |
| Mineral Oil | 5 | 5 | 5 | 5 |
| Steareth-2 | 2 | 2 | 2 | 2 |
| Steareth-20 | 2 | 2 | 2 | 2 |
| Water | qsp 100 | qsp 100 | qsp 100 | qsp 100 |
| pH | 10.7 | 10.7 | 10.7 | 10.7 |
| Curl Efficiency | Good | Very Good | Very Good | Poor |
| Curl Number | Good | Good | Very Good | Good |
| Volumizing and Styling Effects | Good | Good | Good | Fair |

Evaluations 1 g of each composition was applied on 1 g of a pre-shampooed Chinese hair swatch, and the hair was wound onto a 16-mm perm rod and covered by a physical wrap of a plastic film, and then heated by a digital processor (OOHIRO ODIS EX) for 10 minutes at 90° C. After removing the physical wrap, the hair on the rod was cooled at ambient temperature for 5 minutes and removed from the rod. The hair was then rinsed with tap water, the curl shape was aligned, and the hair was dried in an oven.

The curl efficiency and the curl number of the curled hair were evaluated as follows.
(Curl Efficiency)

The value of $(L_0-L)/L_0$ (wherein $L_0$ means the length of hair before curling and L means the length of hair after curling) was determined for each of the hair swatches by measuring the length of the hair before and after curling, and the determined value was evaluated in accordance with the following criteria.
Very Good: Equal to or more than 0.16
Good: Equal to or more than 0.13 and less than 0.16
Fair: Equal to or more than 0.11 and less than 0.13
Poor: Less than 0.11
The results are shown in Table 2.
(Curl Number)

The number of curls was counted for each of the hair swatches, and evaluated in accordance with the following criteria.
Very Good: Equal to or more than 11
Good: Equal to or more than 9 and less than 11
Fair: Equal to or more than 7 and less than 9
Poor: Less than 7
(Volumizing and Styling Effects)

The volumizing and styling effects of the side to which the composition had been applied were evaluated just after styling and after 8 hours by two expert panels in accordance with the following criteria.

Good: More volume compared to the untreated side and the benefit lasted for 8 hours or more Fair: More volume compared to the untreated side but the benefit decreased after 8 hours The results are shown in Table 2.

As shown in Table 2, a combination of pentylene glycol and ethanol improved curl performance as well as volumizing and styling effects. In addition, the mixture of these solvents with a certain ratio showed further better performance.

The invention claimed is:

1. A process for reshaping keratin fibers comprising:
   (i) applying onto the keratin fibers a composition comprising pentylene glycol and at least one monovalent alcohol, wherein the composition has a pH ranging from 8.0 to 13.5, and wherein the composition is free of a reducing agent; and
   (ii) heating the keratin fibers after applying the composition onto the keratin fibers.

2. The process according to claim 1, wherein the composition has a pH ranging from 9.0 to 11.0.

3. The process according to claim 1, wherein the amount of pentylene glycol in the composition ranges from 0.01% to 20% by weight, relative to a total weight of the composition.

4. The process according to claim 1, wherein the amount of pentylene glycol in the composition ranges from 1% to 10% by weight, relative to the total weight of the composition.

5. The process according to claim 1, wherein the amount of the at least one monovalent alcohol in the composition ranges from 0.01% to 20% by weight, relative to the total weight of the composition.

6. The process according to claim 1, wherein the weight ratio of the amount of pentylene glycol to the amount of the at least one monovalent alcohol in the composition ranges from 0.1 to 10.

7. The process according to claim 1, wherein the weight ratio of the amount of pentylene glycol to the amount of the at least one monovalent alcohol in the composition ranges from 0.3 to 3.

8. The process according to claim 1, wherein the composition further comprises at least one alkaline agent.

9. The process according to claim 8, wherein the at least one alkaline agent is selected from inorganic alkaline agents other than ammonia.

10. The process according to claim 8, wherein the at least one alkaline agent is selected from alkaline metal hydroxides.

11. The process according to claim 1, wherein the composition further comprises at least one organic acid.

12. The process according to claim 11, wherein the at least one organic acid is a monovalent organic acid.

13. The process according to claim 1, wherein the process comprises waving the keratin fibers.

14. The process according to claim 1, wherein the keratin fibers are heated during the heating step at a temperature ranging from 50° C. to 180° C.

15. The process according to claim 1, further comprising a step of placing the keratin fibers, before the heating step, in an occlusive space surrounding the keratin fibers.

16. The process according to claim 1, further comprising a step of rinsing and/or drying the keratin fibers following the heating step.

* * * * *